United States Patent
Berg, Jr. et al.

(10) Patent No.: US 6,958,057 B2
(45) Date of Patent: Oct. 25, 2005

(54) TAMPON APPLICATOR ARRANGEMENT

(75) Inventors: Charles John Berg, Jr., Wyoming, OH (US); Andrew Lloyd Bouthilet, Cincinnati, OH (US); Jacqueline Ann Daniels, Fairfield, OH (US); Peter Worthington Hamilton, Cincinnati, OH (US); Caroline Stoney Simons, Cincinnati, OH (US); Richard Tweddell, III, Cincinnati, OH (US); Glen Charles Fedyk, Fairfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 299 days.

(21) Appl. No.: 10/152,598

(22) Filed: May 21, 2002

(65) Prior Publication Data

US 2003/0028177 A1 Feb. 6, 2003

Related U.S. Application Data

(63) Continuation-in-part of application No. 09/923,082, filed on Aug. 6, 2001, now Pat. No. 6,610,025.

(51) Int. Cl.[7] .................................................. A61F 13/20
(52) U.S. Cl. ............... 604/385.17; 604/11; 604/385.18; 604/14
(58) Field of Search ........................ 604/11–18, 385.17, 604/385.18, 57–60

(56) References Cited

U.S. PATENT DOCUMENTS 2,413,480 A * 12/1946 Winter
2,828,832 A    4/1958 Spiess et al.
3,499,447 A    3/1970 Mattes et al.
3,674,025 A    7/1972 Bleuer
3,760,808 A    9/1973 Bleuer
3,791,385 A    2/1974 Davis et al.
4,312,348 A    1/1982 Friese
4,610,659 A    9/1986 Friese
5,569,177 A   10/1996 Fox et al.
5,693,009 A   12/1997 Fox et al.
5,766,145 A    6/1998 Fox et al.
5,817,047 A   10/1998 Osborn
5,827,214 A   10/1998 Fox et al.
5,928,183 A    7/1999 Fox et al.
6,068,899 A    5/2000 Osborn

* cited by examiner

*Primary Examiner*—John J. Calvert
*Assistant Examiner*—Jacqueline Stephens
(74) *Attorney, Agent, or Firm*—Bridget D. Ammons; Kevin C. Johnson

(57) ABSTRACT

The present invention relates an arrangement and a process for making the arrangement that comprises a tampon, an applicator unit, and a uniformly shaped film cap. The tampon has a withdrawal end opposed to an insertion end, the insertion end having a top portion. The applicator unit contains at least a portion of a tampon and has a bottom side opposed to a topside. The film cap is uniformly shaped and covers at least a portion of the top portion of the tampon and attaches to at least a portion of the applicator unit. The arrangement is obtainable by a process comprising the steps of attaching the planar film to the applicator and shaping and or stretching the planar film to create a film cap.

8 Claims, 4 Drawing Sheets

TAMPON APPLICATOR ARRANGEMENT

CROSS REFERENCE TO RELATED APPLICATION

This is a continuation-in-part of application Ser. No. 09/923,082 filed on Aug. 6, 2001. Now U.S. Pat. No. 6,610,025.

FIELD OF THE INVENTION

This invention relates to tampon applicator arrangement having a film cap positioned over the tampon and a process for making such an arrangement

BACKGROUND OF THE INVENTION

Many configurations of applicators are currently commercially available including applicators with either open-ended inserter tubes and those with petals on the inserter tube. When users insert opened and petal applicators, users may find that the open edge or petals edge may scrape the vagina, labia or other tissues. As well, when users insert open-ended applicators the exposed head of the dry tampon may drag against the skin making insertion uncomfortable. Many attempts have been made to provide easier, smoother, and comfortable insertion and removal of applicators. It was discovered that in order to provide a smooth and safe insertion of the tampon, a film cap on an applicator must rupture on a specific moment, when a low, maximum force is applied, while maintaining attachment of the film cap so that the arrangement does not leave residue in the body. The superior design of the present invention will achieve these goals, as will be seen from the following discussion.

BACKGROUND ART

U.S. Pat. No. 3,760,808 issued to Keith T. Bleuer relating a TAMPON APPLICATOR ASSEMBLY.

SUMMARY OF THE INVENTION

The present invention relates an arrangement and a process for making the arrangement comprising a tampon, an applicator unit, and a uniformly shaped film cap. The tampon has a withdrawal end opposed to an insertion end, the insertion end having a top portion. The applicator unit contains at least a portion of a tampon and has a bottom side opposed to a topside. The film cap is uniformly shaped and covers at least a portion of the top portion of the tampon and attaches to at least a portion of the applicator unit The arrangement is obtainable by a process comprising the steps of attaching the planar film to the applicator and shaping and or stretching the planar film to create a film cap.

BRIEF DESCRIPTION OF THE DRAWINGS

FIG. 3b is a cross sectional view of the arrangement of FIG. 3a.

DETAILED DESCRIPTION OF THE INVENTION

Figure 1A:
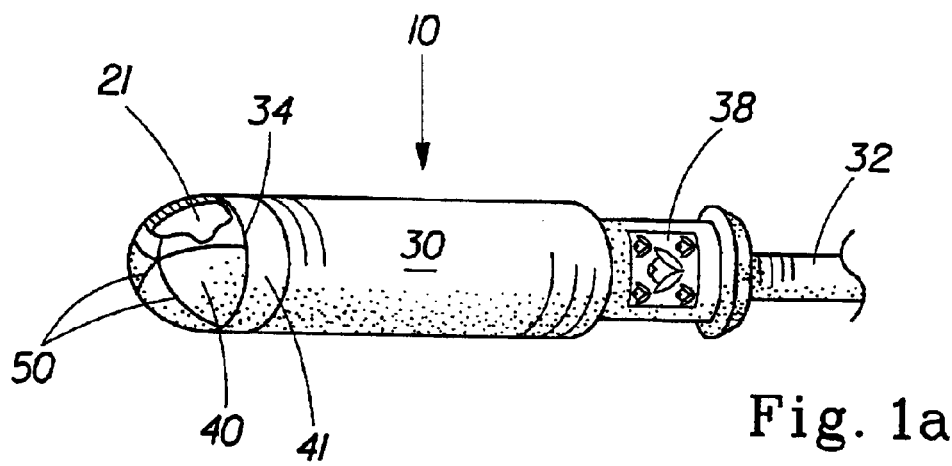
FIG. 1a is a perspective view of a typical arrangement of the invention.

All documents cited are, in relevant part, incorporated herein by reference; the citation of any document is not to be construed as an admission that it is prior art with respect to the present invention As used herein "anvil" refers to a structure generally the size and shape of a tampon, used to create areas of weakness in the film cap after the film cap is attached and shaped. The anvil may be textured or patterned or it may be smooth. In most embodiments, the anvil acts like cutting board for a separate tool that is used to create areas of weakness. The anvil may be the tampon itself and may include re-useable or disposable materials including but are not limited to metals, composite materials, laminates, plastics, polymers, engineering materials, sintered structures, porous structures, solid porous structure, cellulosic materials, and wood. The anvil may provide additional functions such as vacuum transmissions, air pressure blow-off transmission, electrical current or potential electric retention, magnetic attraction or repulsion, additive or lubricant or medicant transfer to the film cap.

As used herein "applicator" refers to a mechanism that facilitates the insertion of a tampon into the vagina of the wearer. Any known hygienically designed applicator may be used for insertion of a tampon, including the so-called telescoping, tube and plunger and the compact applicators. The applicator may be one or more units. In one example, the inserter tube may be 66 mm long and have an internal diameter of 15 mm. The pusher tube may have a length of 73 mm and an external diameter of less than 15 mm.

The term "areas of weakness" refers to areas of varied thickness typically located on the film cap portion which are thinner compared to other areas of the film cap that may facilitate the rupture of the film cap while providing fully hygienic coverage of the tampon top. The areas of weakness may have a pattern, such as thin lines, perforations, slits, spots or combinations thereof and may be in any shape, including straight or curved or zigzag and in any direction The areas of weakness may be present in the film prior to or subsequent to shaping the film cap. Lines of weakness may divide the film cap in petals by running from the top of the film cap toward the attachment region of the film cap. The film cap can be divided into any number of petals often 2, 3,4,5,6 or 7 petals, and most typically forming 3,4 or 5 petals. In other embodiments, the top portion of the film cap may open along one line but not preferably a single line divides the film cap in two symmetrical halves. As well, it is not desirable for a film cap to have a single a single rupture line near the bottom of the film that is attached to the applicator, so that rupture pattern can result in a top portion 'lid' remaining peripheral section of the attachment acts like a 'hinge.'

The "arrangement" comprises a tampon, an applicator unit and a film cap.

For the purpose of the invention, "average maximum film cap extension" is the average distance calculated between the rupture line on the top portion of the film cap and the topside of the applicator unit when the film cap is at its maximum stretch just prior to rupture that is measured as described below.

The term "delamination" refers to a process of unwrapping or unwinding of the paper layers of an applicator unit in the toilet bowl or sewer systems, which improves the flushability of the applicator unit.

As used herein "film cap" refers to the structure positioned over or on the top portion of the tampon, and/or the corresponding part of the applicator unit (topside). The film cap herein may have a top portion that is typically dome shaped and corresponds to the top portion of the tampon and/or the topside of the applicator at the attachment region that is referred to as the collar potion. The film cap may be attached to the applicator unit containing the tampon at any position including the topside, bottom side, interior or exterior and is typically not attached to the tampon. Film caps can be attached to both open-ended applicator units and applicators with segments or petals.

The term "hoop stress" is the force exerted perpendicular to the radius in a cylinder or circle.

The term "joined" or "attached" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element; I.e., one element is essentially part of the other element.

The "maximum expulsion force" refers to the highest force observed during full-intended expulsion of the tampon, as measured independent or outside of the human body. The maximum expulsion force combines all force aspects of the arrangement, including the force necessary to rupture and expel the tampon through the film cap as well as other factors such as friction between the tampon and applicator unit.

The phrase, "no welds or seams" applies to the film prior to shaping it into a film cap with a mold, and to the resulting cap, prior to attachment "No welds or seams" does not apply to the film cap subsequent to attachment to the applicator that may include a welding step.

As used herein the term "rupture" refers to the tearing of breaking of the film cap that allows the tampon to be inserted within the vagina. "Rupture line" is a mark that indicates the location of the break in the film cap.

As used herein the term "tampon" refers to any type of absorbent structure that is inserted into the vaginal canal or other body cavities for the absorption of fluid there from, or for the delivery of active materials, such as medicaments, or moisture. Tampons are generally "self-sustaining" in that they will tend to retain its general shape and size before use. The tampon has a withdrawal end opposed to an insertion end having top portion. A tampon may be straight or non-linear in shape, such as curved along the longitudinal axis. A typical compressed tampon is 40–60 mm long, the length measured from the top portion to the withdrawal end along the longitudinal axis. A typical compressed tampon is 10–16 mm wide corresponding to the largest cylindrical cross section although the width may vary along the length.

A portion of the film cap or the entire film cap is "uniformly shaped". As used herein "uniformly shaped" refers to the surface of the film cap in relation to the top portion of the tampon and the topside of the applicator. The film cap generally conforms to the shape of the top portion of the tampon or topside of the applicator unit, having the smallest possible surface area.
If the top portion of tampon or the topside of the applicator has one or more gaps, the film cap may or may not be shaped into those gaps in order for the film cap to conform to the smallest possible surface area, but remains parallel to the surface of the gap and remains in contact with the tampon or applicator. Uniformly shaped also means that the film cap has no rugosites, such as loose folds or wrinkles, other then optional tension wrinkles, and there are also no seams and/or welds. The film cap's collar portion is typically substantially smooth and the top portion of the film cap is also substantially free of wrinkles.

As used herein, "cm" is centimeter, "dpf" denier per foot, "g" is grams, "gms" is grams per square meter "mm" is millimeters, "ml" is milliliters, and "sec" is seconds.

The following is a description of typical arrangements of the invention, referring to the Figures. FIG. 1a shows an arrangement 10 in perspective view. The applicator has a first applicator unit 30 with a finger grip 38, and containing also a plunger or pusher part 32. Inside the first applicator unit 30 is a tampon 29 viewed through a cut out, the tampon having a top portion 21 that partially extends from the applicator unit. A film cap 40 covers the top portion of the tampon 21 and the film cap may be in contact with the entire tampon top portion 21. The film cap 40 extends to collar portion 41, which is attached to the outside of the first applicator unit 30, such that the collar portion 41 forms an attachment region on the applicator unit 30. In FIG. 1a it is shown that the film cap 40 is in contact with part of the first applicator unit 30.

The film cap 40 has, as areas of weakness, 5 lines of perforations 50, and divides part of the film cap 40 into 5 identical film petals. Typically, the lines of perforations 50 are located on the part of the film cap that is in contact with the tampon top portion 21, up to the edge of the collar portion or may extend onto the collar portion 41. In FIG. 1a, the lines of perforation 50 converge at the top of the film cap 40.

Figure 1B:
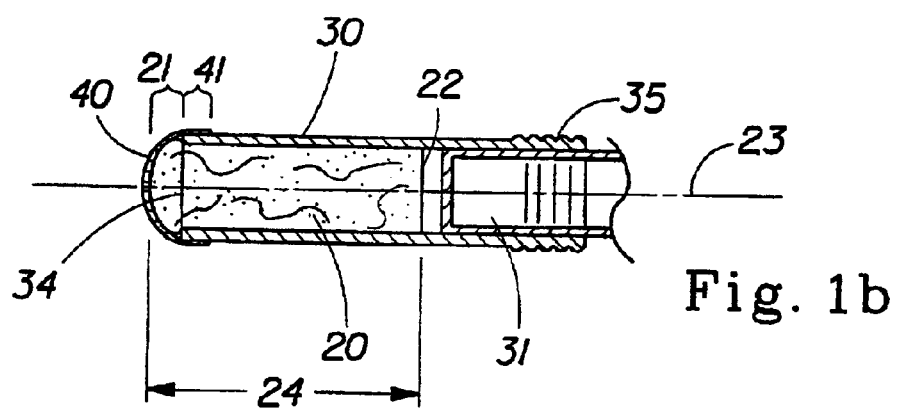
FIG. 1b is a cross-sectional view of another arrangement of the invention.

FIG. 1b shows a schematic cross-sectional view of the top part of another embodiment of the arrangement that has an applicator with second applicator unit 31, whereby the second unit 31 can be pushed inside the first unit 30, to push the tampon 20 out of the first unit In FIG. 1b, only the first applicator unit 30 is filly shown, with the leading portion of the second unit 31 depicted inside a portion of the first unit 30 in the end where the grip 35 is located. The tampon has a tampon top portion 21, which extends from the leading edge or top edge 34 of the first applicator unit 30. The tampon 20 and applicator unit 30 have each a longitudinal axis, along line 23 and the tampon has a length 24, which equals the distance from the point where the longitudinal axis 23 crosses the top of the tampon 20 to the point where the axis 23 crosses the bottom side of the tampon 22. The part of the tampon exposed in FIG. 1b is the part of the tampon from the leading edge 34 to the point where the longitudinal axis 23 crosses the top of the tampon, which equals here the tampon top portion 21.

Figure 1C:
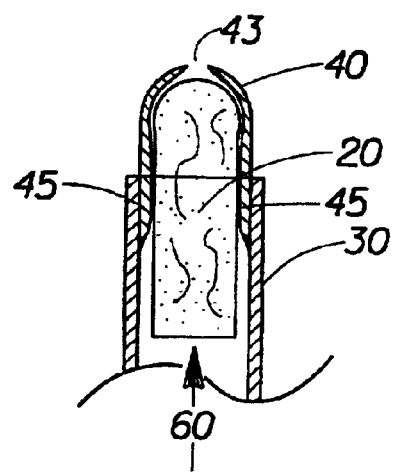
FIG. 1c is a cross-sectional view of an arrangement as in FIG. 1b in use.

In FIG. 1c, a part of the arrangement of the invention is shown, whereby the film cap is attached with attachment areas 45 to the interior of the applicator unit 30, partially shown. The film cap 40 conforms to the tampon 20, up to the point it is attached to the applicator unit 30. When the tampon 20 is pushed out of the first applicator unit 30 with a force applied from the bottom, along force line 60, the film cap 40 may extend before it forms the first indication of a rupture line 43. The average maximum film extension is measured up to the point 43.

Figure 2A:
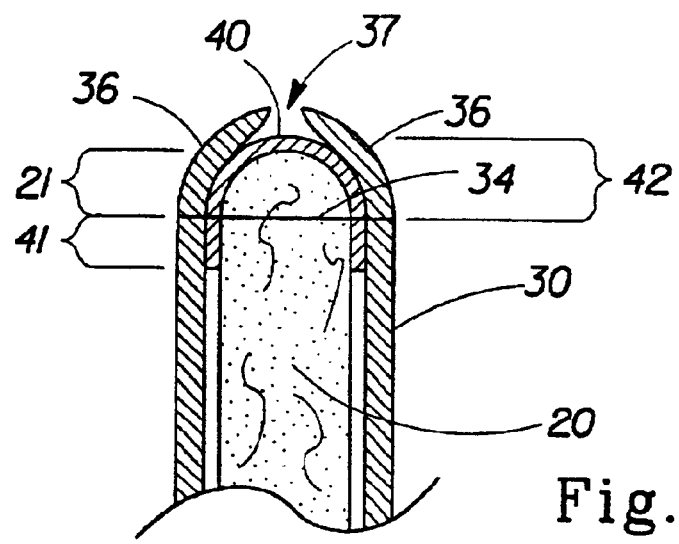
FIGS. 2a and 2b are a cross-sectional view of other typical arrangements.

Once the film cap 40 ruptures, the tampon 20 leaves the first applicator unit 30 generally under a reduced pushing force. FIG. 2a shows a cross sectional view of part of an arrangement of the invention with an alternative film cap 40 construction and an alternative first applicator unit 30 construction that is partially shown. The first applicator unit 30 has a number of applicator petals 36, which extend from the line 34 of the unit 30, this line 34 being the horizontal line through the bottom edges of the petals 36. The petals 36 converge almost above the top of the tamp 20, leaving a small gap 37 at the top. When the tampon 20 is pushed upwards, the petals 36 open, to let the tampon through, into the vagina.

The film cap 40 is formed over the tampon 20, or inside the applicator unit 30 and thus lays between the tampon 20 and the applicator unit 30. At least the top portion 42 of the film cap 40 is in contact with the entire tampon top portion 21 (part of the tampon 20 extending beyond the line 34 of the first unit 30), and is thus uniformly applied.

Figure 2B:
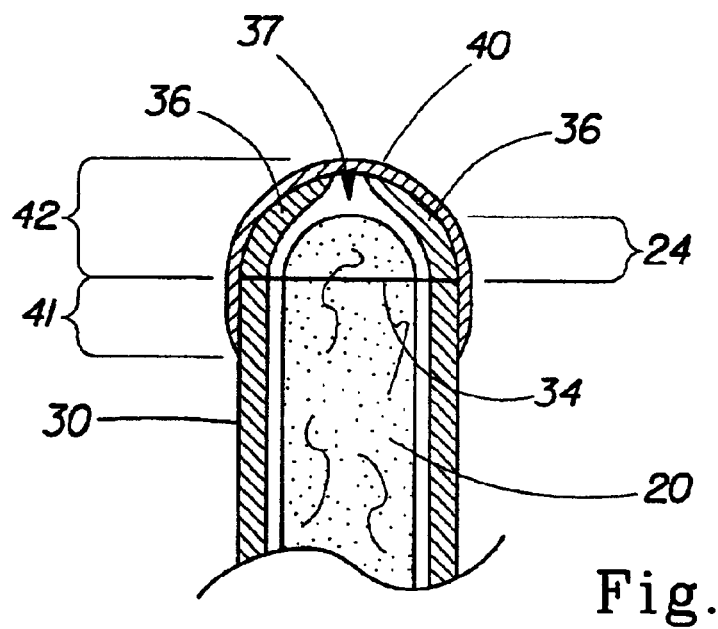

The collar portion 41 of the film cap is attached to the inner wall of the first applicator unit. FIG. 2b shows a cross sectional view of part of an arrangement of the invention with an alternative film cap 40 construction, compared to FIG. 2a. The applicator unit 30 has again a number of applicator petals 36, extending from the line 34 of the unit 30. The film cap 40 is positioned over the unit 30 and the petals 36.

Figure 3A:
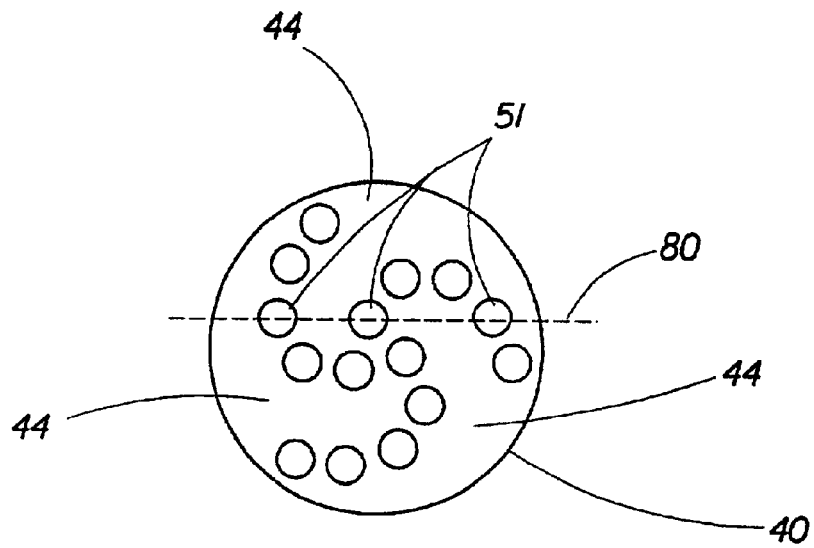
FIG. 3a is a top view of a typical arrangement of the invention.
Figure 3B:
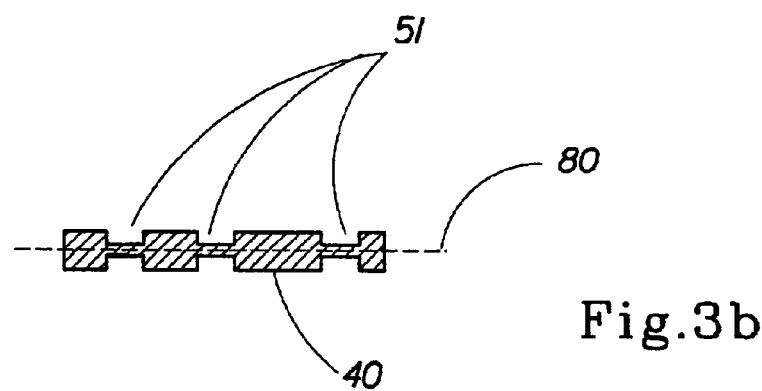
Figure 3C:
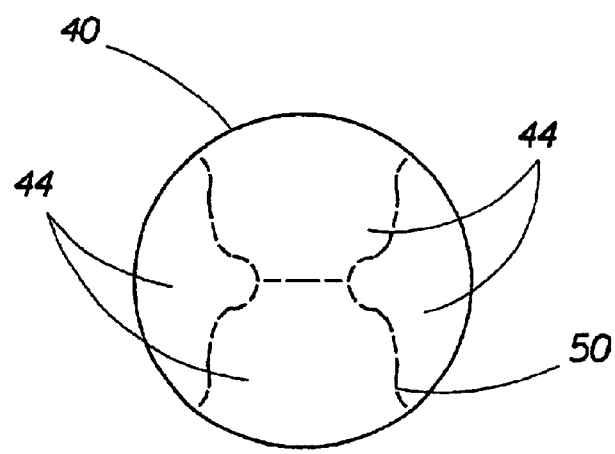
FIG. 3c is a top view of another arrangement of the invention.
Figure 4:
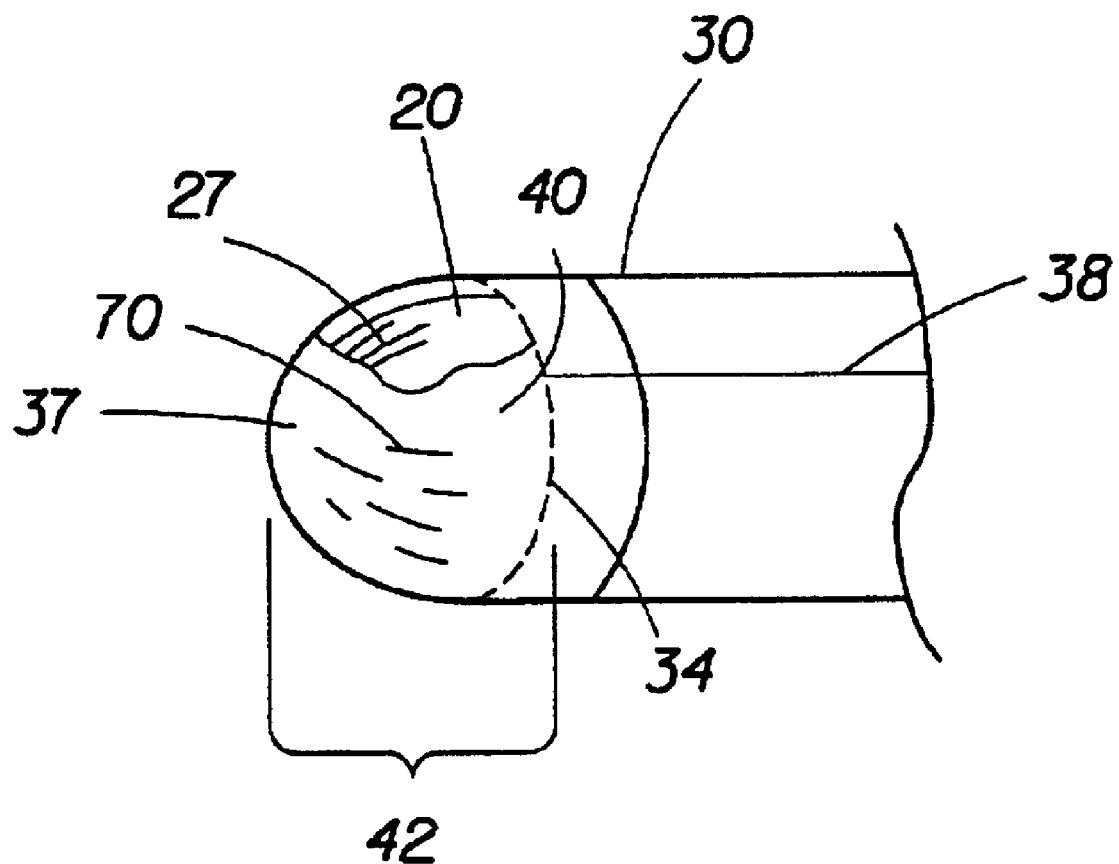
FIG. 4 shows a perspective view of the top portion and part of the collar portion of a typical film cap and the tampon and applicator unit.

In the area where the film cap 40 is present, the film cap 40 is in contact with the entire applicator unit 30, except of course where there is a gap 37 in the top of the applicator unit 30. Thus, for the purpose of the invention, the film cap 40 is uniformly shaped onto the applicator unit 30. The collar portion 41 of the film cap is attached to the outer wall of the first applicator unit 30, by any method described herein or generally known. FIG. 3a shows a top view of an alternative film cap 40, having lines of weakness in the form of lines of thinned areas 51, in this case in a spiral configuration. The lines of thinned areas define film cap petals 44, which will detach from one another, to thus provide the film cap 40 to rupture. FIG. 3b shows a cross sectional view of the film cap 40, along the cross section line 80 in FIG. 3a showing the thickness variations therein, and showing the 3 thinness areas 51 which lie on the cross section line 80. FIG. 3c shows another top view of an alternative film cap 40, having lines of weakness in the form of perforations 50, defining film cap petals 44 of different width and length The petals 44 will detach from one another, to thus provide the film cap 40 to rupture. FIG. 4 shows a perspective view of a part of the arrangement of the invention. The open-ended applicator unit 30 has a gap line 37, running longitudinally along the side of the unit 30, which is covered by the film cap 40, which is attached thereto (a part of the collar portion of the film cap 40 is shown). The film cap 40, positioned over the gap 37 in the applicator unit 30 is uniformly shaped, because it is such that it has the smallest possible surface area over the applicator unit 30, namely it is stretched under tension over the applicator unit 30 and does not follow the gap 37 in the unit.

The tampon top portion 21 (from the top of the tampon 20 to the leading edge 34 of the applicator unit 30) is also covered by the uniformly shaped film cap 40, or in fact the top portion 42 thereof. The tampon 20 has also one or more gaps 27, running from the top of the tampon 20 towards the edge 34 of the applicator unit 40. The film cap top portion 42 is uniformly shaped, because the film cap top portion 42 is in contact with the surface of the entire tampon top portion 21, including (part of) the gap 27. The film cap top portion 42 thus follows the gap area 27 of the it, tampon top portion 21.

The top portion 42 of the film cap 40 has a small tension winkle, 70, due to the formation of the film cap 40, which is done by stretching a film material over a male mold or in a female mold, and due to the fact that the top surface of the tampon has some irregularities and the film cap 40 is attached to the applicator unit 30 under the shaped tension, resulting in tension wrinkle 70. The tension wrinkle 70 may be removed by an additional process step as described herein below. However, because the wrinkle 70 hardly extends from the surface of the tampon top portion 21, and because it is under tension, it does not create any harm during insertion, or problems for the expulsion of the tampon 20 through the film cap 40.

I. The Tampon of the Present Invention

The tampon of the present invention may be constructed from a wide variety of liquid-absorbing materials commonly known in the art and used in absorbent articles such as rayon (including tri-lobal rayon structures such as GALAXY Rayon available as 6140 Rayon from Acordis Fibers Ltd., of Hollywall, England and conventional rayon fibers, and needle punched rayon), cotton (long fibers, short fibers, cotton linters, T-fibers, card strips, comber cotton), or comminuted wood pulp.

II. The Applicator of the Present Invention

Applicators may be open ended or have inwardly tapering flexible segments or petals at its top portion to form a normally closed, smooth, openable top. Some examples of applicators that may be used are shown in the Figures. The applicator may be made of plastic, paper, cardboard, degradable or compostable thermoplastic materials, typically water dispersible or water soluble materials, biodegradable materials, and other materials known in the art. For example, a tampon applicator can be constructed of a spiral-wound paperboard construction and coated on the exterior with a coating material, such as wax. Applicators may be flushable through the toilet or discarded in the trash III. The Film Cap of the Present Invention The film cap of the present invention is typically molded such that its shape and dimension conform to the top portion of the tampon and/or the topside of the applicator, thus the film cap dimensions are about the same as top portion of the tampon and/or the topside of the applicator. The film cap of the present invention may be used with open ended applicators or applicators with petals. In some embodiments the film cap may be under the petals positioned between the petals and the tampon top portion. In other embodiments, the film cap is positioned over the petals, just covering the area of the petals, or the area of the applicator top where the petals do not cover the tampon at the gap, or both However, many embodiments include arrangements that are open ended. In an open-ended embodiment the top portion of the film cap extends over the topside of the applicator unit and the collar portion of the film cap is attached to the applicator.

a. Film

The film cap may be made of any type of planar, flexible film or other deformable substrate. The typical film material used to make a film cap may be a sheet-shaped substrate that may smooth or embossed Some materials include paper, woven and non-woven substrates, cloths, metal foils, cellulose fibre sheets, and organic polymeric materials.

Film materials may be single layer, planar laminate or comprise connected structures of two or more film materials joined to each other in a horizontal side-by side arrangement, for example lap or edge-to-edge butt joints to form the film. Such joined materials may leave a weld or seam, though care should be taken to minimize the length, width and height of such welds. Generally the welds may be flattened out, or covered by a coating, prior to use of the joined film to make the film caps. In typical embodiments of the invention, the film used to make the film cap has no welds or seams.

Films may be made of one or more of the following substrates and resins: polyolefins, cellulose materials and derivatives, including cellulose ethers, ethyl and/or methyl celluloses, cellulose esters, including cellulose acetates, and/or formates, vinyl polymer derivatives, or more typically cellophane and/or polyethylenes, polypropylenes, PET, PVC, latex, nylon, polyesters, polystyrenes. Some other resins and films include polylactides, polyester amides, aliphatic esters, aliphatic-aromatic copolyesters, polyhydroxyalkonoates, polyalkulene succinate, polyvinyl alcohols, cellulosic polymers, starch-based materials and/or polycaprolactone. Polyolefin, such as polyethylenes and polypropylenes and/or biodegradable films are typical. Polyclefins are also described and defined in "*Plastics and Films*", chapter 2, by *J. H. Briston, 3$^e$ edition*, published in 1988, Langman Scientific & Technical.

Some film and resin examples are: BAK 1095 (available from Bayer), Eastar Bio (available from Eastman Chemicals) for example a blown 37 micron Eastar Bio film, Mater-Bi (available from Novamont), Biomax (available from DuPont), Bionelle (available from Showa High Polymer), Lunare SE (available from Nippon Shokubai), EcoPLA (available from Dow Cargill), Exoflex (available from BASF), Biotec (available from Kashoggi), Vinex (available from Air Products), cellophane (available from UCB films including the low stretchable or low yieldable uncoated cellophane of about 24.3 microns thick), LACEA (available from Mitsui), and HDPE film available from Tredegar.

Typical olefin films include in particular linear low density polyethylenes (LLDPE) and low density polyethylenes (LDPE) as available from Clopay and high density polyethylenes (HDPE) as available from Tredegar, including for example LDPE film of 25 microns nominal thickness, called DH215 available from Clopay.

The film and the film cap may be porous, micro-porous, or non-porous. The film and film cap may be gas and/or water permeable. The film and film cap may have a low or high critical surface tension. The film and film cap may be hydrophobic or hydrophilic, thernoplastic, and/or thermosetting, or even water soluble, water-disintegratable, or water-dispersible. The film and film cap may shrink upon exposure to heat or application of pressure or vacuum. Some films that exhibit these qualities are single or biaxially oriented films, such as polypropylenes.

The film used to make the film cap may be made by any process known in the art including casting, extrusion, or blown extrusion processes. The film and film cap may have a functional coating on one or each surface that may change the film's properties such as hydrophilicity, hydrophobicity, coefficient of friction, heat sealing properties, gas and/or water permeability, colour, tactile feel and/or odour.

The film may be a highly extensible film. Highly extensible film has an elongation at break in the machine direction of at least 150%, typically from 200% to 1000%, or even from 350% to 850%. Typically, the elongation at break in the cross-machine direction is in the same range as mentioned above. An example of a typical material is polyethylene DH215, available from Clopay, which has an elongation at break in machine direction of about 630% and in cross machine direction of about 765%. The percentages are average percentages of at least 5 samples. A person skilled in the art is using ASTM D882 can easily determine the elongation at break.

b. Film Thickness

The film typically has an initial thickness that may be homogenous or varied prior to formation of the film cap and is between 1 and 200 microns. The thickness may be from 5 to 100 microns, 10 to 75 microns, 15 to 50 microns or most typically from 20 to 40 microns. This film thickness is the calliper, measured as set out herein.

Variations in film thickness, can be created by a multitude of techniques including use of embossing the film during manufacturing, applying a coat extrusion of varying thickness to a base film, creating a film from two or more substrates of different thickness or joining together films. The variation of film thickness from one area to the next that may be large or small. The areas of weakness may be located in at least partially, or only on the top portion of the film cap. For example, the areas of varied thickness are typically less than about 5%, about 3%, about 1% or even less than about 0.5% of the total surface of the film cap.

Comparing the thickness of part of the film cap to the original thickness of the film, there is typically at least an area of the film cap where the thickness is at least 10% less than the original film thickness. In measuring the calliper in the film cap, the thickness variation from one area to a second area may be at least about 10%, about 20%, about 40%, about 60% or even at least about 80%. Generally, variations in thickness may be at least about 20% from one area to a second area. Film thickness may vary from between the top portion and the collar portion and in some embodiments, the top portion is thinner tan said collar portion. In typical embodiments, the collar portion is thinner than the top portion. The variation in the thickness of the cap can be measured by any suitable known. For large areas, a calliper gauge may be suitable, or method as described in U.S. Pat. No. 6,231,556. For smaller areas, a more microscopic technique is required, for example embedding the film cap in a setting resin, making thin cross section slices of this embedded film cap and measuring the thickness or gauge of the film cap in this cross section by use of for example a scanning electron microscope (SEM). The film may have breaches that have no thickness and single or multiple breaches. Breaches may include holes, perforations, slits, gaps, voids, openings, punctures, cracks, apertures, pores, etc.

IV. The Tampon and Applicator Arrangement of the Present Invention

In all embodiments of the arrangement the film cap is in close proximity and is parallel with the top portion of the tampon and the topside of the applicator unit. In many embodiments, the film cap is in contact with applicator unit or tampon so that distance between the entire film cap and the applicator unit or tampon is zero.

a. Average Maximum Film Cap Extension:

The average maximum film cap extension is a measure of how far the film cap stretches before it ruptures. The moment of the maximum film cap extension is observed by, as the tampon pushed through the applicator unit, camera and/or recorded video and is typically the moment of rupture of the film cap. The average maximum film extension is the distance measured from the highest point of the edge of the applicator unit to the rupture line, and it can be presented as a percentage of the total tampon length. If the film ruptures along an uneven line, so that the film cap thus has a non-uniform length at the moment of rupture then the average length of the film cap at this moment is taken to equal the point, referred to above.

For example, for an arrangement with a tampon which has a total length, from the flat bottom withdrawal end to the top of the rounded top portion of 6 cm, and an average maximum film cap extension (average length of rupture line to edge of applicator unit) of 2.0 cm, the percentage tampon exposed as defined herein is (6 cm−2.0 cm)/6 cm×100%= 66.6%. In one embodiment of the invention, the arrangement is such that it has at least 20% of the tampon exposed beyond the point of average maximum film cap extension. For purposes of the present invention, the average maximum film cap extension can be readily determined by pushing the tampon from the applicator unit with a constant speed while recording the time of the start of the pushing of the tampon ($t_0$) and the time of the film cap ruptures, which is observed as above ($t_r$ i.e. the first instance that the film forms a rupture), and then, the average point (length) of maximum film cap extension/rupture can be calculated from the elapsed time $t_r-t_0$ and the known speed, and the percentage tampon exposed can be calculated as above.

Typically this percentage is at least 30% or even at least 40% or in certain embodiments herein, even at least 50%, or even at least 60%.

It is beneficial for a film cap to be formed by stretching a stretchable plastic yieldable film that can be uniformly shaped and can provide a high percentage of tampons exposed beyond maximum film cap extension during tampon expulsion, which typically requires only a low expulsion force. Therefore, a typical embodiment of the invention is an arrangement that has a film cap that is made from a stretchable plastic yieldable film that typically requires only a low expulsion force. Typically the resulting film cap is less plastically extensible or stretchable than the film. The use of such a stretchable or plastic yieldable film, may allow for about 50%, about 60%, about 70% or more than about 80% of the tampon to be exposed at the maximum film cap extension. These results may also be achieved by making a film cap from a stretchable plastic yieldable film and subsequently submitting the formed film cap to a step to reduce the stretchability, for example, a strain-hardening step to induce plastic yielding. In the case when the film cap is strain neutral or strain hardening during extension/tampon travel, the force increases when the film is more extended, reaching the maximum force when the film ruptures.

b. Maximum Expulsion Force:

The maximum expulsion force typically occurs at the moment the arrangement reaches the point of maximum film cap extension. However this maximum expulsion force may occur prior to the rupture of the film cap, such as is the case if the film cap is strain softening. The maximum expulsion force and the concurrent observation of the moment of rupture of the film may be determined by placing a arrangement of the invention in a device employing a Dillon Force Gauge (Mecmesin AFG50N) or similar gauge, which can measure the peak force or "maximum expulsion force." The measurement is done by following the procedures in the operating manual of the device concerning how to measure the peak force.

The force gauge is oriented such that the load cell 'foot' will travel in the horizontal direction, and it is mounted to a stand and it remains stationary during the test. A propelled, movable horizontal slider is affixed to the stand to one side of the force gauge and is controlled by a linear actuator. An anchored applicator clamp with an internal diameter set to correspond to the diameter of the applicator is attached to the slider. The clamp is used to hold the inserter unit of the applicator stationary during the test without deformation of the applicator.

When using a telescoping tubes arrangement the inserter tube is anchored to the slider by the applicator clamp, the push tube is still free to slide within the inserter tube. The slider and force gauge are so aligned on the stand that the push tube's longitudinal axis and the force gauge's load cell axis are in-line with each other, in this case a horizontal line. The non-expulsion end of the push tube is positioned to face the load cell 'foot'.

When the slider is actuated, it will move the arrangement towards the load cell foot. The measurement is done at a constant speed setting of the device; a speed of 7.5 cm/sec is an exemplary speed for the test of the arrangements of the invention. When the slider engages the end of the push tube against the load cell foot, the push tube stats its travel within the inserter tube, first engaging the bottom of the tampon and then expelling the tampon through the film cap. All the while, the force gauge measures the expulsion force, as well as captures the peak expulsion force. The slider stops its movement towards the force gauge after expelling the tampon from the applicator by the operator manually turning off the slider power source or using some other form of control that can cut the power.

The device will give a reading for the maximum expulsion force. By coupling the device to a timer, the time of the start of the experiment defined for calculation purposes as the time the push tube initially engages the bottom of the tampon, and the time of rupture are monitored, thereby, the extension of the film cap at the moment of rupture can also be calculated. For the arrangements of the invention, the maximum expulsion force is typically below 2500 grams-force, below 2000 grams-force, below 1500 grams-force, below 1000 grams-force or even below 700 grams-force. Generally, the arrangement has a maximum expulsion force from about 700 grams-force to about 2500 grams-force to rupture the film cap and expel the tampon through the film cap. As a general observation, the maximum expulsion force of the arrangement has been found to be even lower when a female molding process is used to form the cap, versus a female molding process, as both described hereinafter.

V. The Process of Making the Arrangement of the Present Invention

The process for making the arrangement cap involves attaching and shaping a planar film into a film cap.

a. Attaching the Film Cap:

The process comprises the step of attaching the film cap to the applicator by any method. The film cap may be securely attached to the applicator by any securing means including heat seals, and adhesives and may be secured in one point, several points, or across a broad area. It is beneficial that the securing means may be able to withstand a percentage of the average maximum expulsion force of the arrangement including at least about 125%, at least about 150%, or at least about 175% of the average maximum expulsion force of the arrangement.

Methods of mechanical attachment include puncturing or embedding parts of the film cap into the applicator, using mechanical fastening means including the hoop stress of the film cap itself, elastic or adhesive tabs or bands. Some process steps to attach the film cap to the applicator involve wetting, or heating the film or both heating and wetting in at least the area to be attached to the applicator. The film cap or film may also be attached by use of an adhesive or cohesive, epoxy bonding, use of pressure, or even allowing a coating on the applicator. For example, wax may be absorbed by or intermingled with pores of the film cap.

The film or film cap may be attached prior to, simultaneous with or subsequent to film cap shaping. The film or film cap may be attached to any internal or external part of the applicator. The film cap needs to be first positioned before attachment, over or into a portion of the applicator and the tampon's insertion end if present Positioning of the film cap may include movements such as bringing the cap next to a portion of the applicator and/or tampon, sliding or pulling the cap over a portion of the applicator and/or tampon, or rolling the cap onto or over a portion of the applicator and/or tampon.

Rolling can include the inversion of the film cap over a portion of the applicator and/or tampon. For example, when the tampon is in the applicator, the part of the film cap that is to correspond to or contact the top of the tampon in the final article is initially brought in contact with the top of the tampon, thereafter the cap is inverted (i.e. turned inside out) while rolling successive regions of the cap down the tampon and applicator surfaces. If desired, the cap can be pre-inverted prior to the inversion process.

The securing means can be checked to confirm that the film cap will not detach inside the body when inserting the tampon by any known method for force determinations. The cap security test is done by attempting to expel a tampon or a likewise shaped object or tool out of the applicator once the portion of the film cap that is not attached to the applicator has been reinforced to prevent rupture. This portion is re-enforced for example with pressure sensitive tape so that it will not rupture when the maximum expulsion force is reached or a multiple of this force is reached, to avoid that rupture takes place prior to release of the film cap from the applicator unit in its attachment point.

To avoid unintended separation of the cap outside the body before use, one can use attachment can use materials and points of attachment to minimize possible peal-off, starting from the base of the collar, up to the top portion of the film cap including attaching a cap collar to the applicator about its periphery.

b. Shaping the Film Cap:

The process comprises the step of shaping the film cap. The film or film cap may be shaped prior to, simultaneous with or subsequent to film cap attachment. The planar film may be shaped with any type of tool that has at least one molding surface that acts to shape a film into a self-sustaining shaped film cap once attached to the applicator. For precision of the process and control of the product quality, it may be typical to shape the film directly over the tampon, applicator, and/or applicator unit However, for practical process reasons it may be typical to use a separate mold for the shaping step. The process of shaping the film over or in a mold may be done by any conventional method including thermo forming, cold-forming and other plastic yield deformation techniques. Cap shaping may occur in a single manufacturing operation. An example of this is creating a film cap that is positioned on or over the tampon of applicator unit and may be optionally further shaped by stretching or strain hardening the film cap.

Molds may be used to shape the planar film. These molds will generally have the shape and dimensions of the tampon or applicator unit including male or female molds of the tampon or the applicator unit, or parts of the tampon or the applicator. The male molding process may be used in some situations because of the accuracy and ease of processing, while the female molding process may be used in other situations because the resulting arrangements can yield lower expulsion forces. The male and/or female or otherwise shaped mold may be provided with a pressure or vacuum source to facilitate the formation of the film cap.

The mold may be air permeable, micro porous, or may comprise small openings such as holes, slits etc. A mold may be made of any material and be externally textured smooth. A micro porous, air permeable mold may be made of aluminium and epoxy aggregate, such as Metapor BF100Al, available from Portec Ltd, Switzerland. Molds may comprise a heat resistant, non-sticky, non-oxidising material including stainless steels and polymers. Molds may be heated or cooled as necessary.

When the film cap is to be attached to the exterior of a cylindrical applicator unit, a mold may be used that is the same size or slightly larger diameter than the exterior diameter of the applicator unit However, the film cap may be stretchable and in such a case a film cap can have a smaller diameter than the exterior of the applicator unit If the film cap is to be attached to the interior of a cylindrical applicator unit, then a mold may have a diameter which is just larger than the diameter of the tampon, and/or smaller than the interior diameter of the applicator unit Part of the mold which forms the top portion of the film cap may comprise more vacuum holes or slits, so that the top portion of the film cap is more thinned, stretched, or plastically yielded than the collar portion of the film cap, resulting in an area of weakness in the top portion of the film cap.

The mold may comprise a separate tool or part of the applicator and/or the tampon itself. The mold can contact and engage the film from either the top or bottom surface of the film. In engaging the bottom surface, the mold can be introduced through the applicator to contact the film.

The female molds and male molds may be used as a 'plug assist' technique. Molds that combine male and female elements may be employed, as an additional means to control the shape formation and/or location and degree of thinned areas. An example is a vacuum male mold, cylindrical in shape with a concave female mold element at the top. The result is a top portion, which is inverted inside the collar portion and is later inverted or pushed outwards to form a convex top portion, and is placed over a dome-shapes tampon or applicator unit. The top portion is then thinned.

The shaping process may also involve plasticizing of the film and/or more typically heating of the film to at least shape the film prior to, simultaneous with, or subsequent to positioning the film in close contact with the mold. For example, the film may be deformable when plasticized with a specific liquid to facilitate the shaping of the film. The liquid may be a plasticizer or solvent for the film. For example, if a film is soluble or is plasticized in water or glycerol then the film may be placed in water or glycerol to make the film deformable for shaping. An example of a film that can be plasticized by water is cellophane that includes also hydrophilic agents such as glycerol.

The film may be deformable when heat is applied and the process involves application of heat. Any source of heat can be used, including placing the film in close contact with a heating element, placing the film through hot air, or using a heated mold.

The process may involve the application of a force onto the film to shape the film such as by plastic yield strain. This process may be combined with heating, dissolving, plasticizing, or wetting the film. The process may be combined with applying air pressure or a vacuum onto the film. For certain plastic yieldable films, a male mold may be used without vacuum employing only mechanical stretching. For a female molding process, it may be typical that a combination of mechanical stretching and vacuum is used, and this may aid creation of weakness areas. It may also aid to anchor the film at different points during the process to cause controlled straining of the film at different points as a mechanical stretch force is applied. Generally, those areas of the film cap that have been stretched or strained via plastic yielding also display a reduced thickness of calliper. The male and female or otherwise shaped mold may be provided with a vacuum source to facilitate the formation of the film cap.

Any excess film may be removed, prior, simultaneous or subsequent to the shaping step or the attachment step. This may be done by any known method, including cutting excess film with a blade, probe, knife, laser, or use of an air or water-knifing step or heated knife or probe.

c. Optional Steps:

Creating areas of weakness: Optionally, the process of making may include the step of creating areas of weakness in the film cap. Areas of weakness may be created prior to, simultaneous with, or and subsequent to film attachment and shaping. The areas of weakness may be made by mechanical puncture, needle punching, mechanical slitting, mechanical embossing, cutting, hydroforming, flame perforating, spark discharge aperturing, vacuum forming, a heated blade, water knifing, hot air perforation, laser perforation/cutting, or ultrasonic energy tools. A vacuum may be unevenly applied on the film so that the film is more stretched and thinned where the vacuum is applied, creating areas of weakness. Such areas may even be sufficiently thinned to actually comprise a breach or breaches in the film cap such as holes or slits. Areas of weakness can be made by any of the above shaping processes alone or in combination.

Areas of weakness can be created after the film cap formation. Such processes may include any of the above shaping process. One process may be a post-formation stretching step, when a film cap is made with a mold and placed on or over a tampon or applicator unit and the film cap is further stretched and thinned. In typical embodiments, the tampon and applicator may be the mold. Areas of weakness can be created by employing an anvil such that the areas of weakness are created while the film cap is in a three-dimensional shaped much like it will be look in the finished arrangement The anvil may be positioned inside the applicator units in a similar position to where the tampon will be located in the finished arrangement The use of the anvil may be such that the anvil is inside the applicator tube prior to perforating or slitting. Areas of weakness may be created after film cap formation by scoring, shearing, slitting, slicing, punching, or perforation with a tool, typically a pin, knife, blade or perforated blades. The tool can be heated or not heated. Typically, the tool will be a heated tool such as a heated blade. For perforated structures where fully cut petals are not desired, the blade area is adjusted via cut-outs, positioning or angle relative to the cap such that land areas remain after the operation. Other methods may include laser perforation/cutting, or ultrasonic energy tools. These methods can be used alone or in combination.

Smoothing: The process may also comprise the additional, optional step of making the film cap or part thereof smoother and free of undesirable wrinkles even after tension, typically the collar portion. This can be done by any method, for example by post stretching as described above, heating part or all of the film cap and/or applying pressure on part or all of the film cap, or further coating part or all of the film cap with another material, such as wax or plastic.

Enabling the Delamination of the Film Cap: As the presence of film caps may inhibit or alter the natural path of delamination of the arrangement in a pool or reservoir of water such as a toilet bowl. Delamination may be facilitated by a number of techniques. One solution that may help facilitate natural delamination of the applicators is dissolution of the film or adhesive used on the film cap. Dissolution of the adhesive allows the film cap to slide off the end of the applicator, leaving the applicator indistinguishable from the traditional cardboard applicator except for a thin coating of adhesive on the outside. In both cases, the arrangement naturally delaminates, as would a traditional cardboard applicator. The exemplary process for making the tampon-applicator does not change except for the use of the water soluble film and/or water soluble adhesive in the production of the present arrangement The soluble film should be such that there is a sufficiently low dissolution within the body to prevent pre-mature break-up or detachment but quick dissolution in a large reservoir of water. Some water soluble films include film made of polyethylene oxide or polyvinyl alcohol. Water soluble film may be used alone or in combination with water soluble adhesive and other processes that facilitate delamination. A layer film with the innermost layer being a water soluble film can be used to achieve the same result as a water soluble film.

Water soluble adhesives can be used alone or in combination with water soluble film and other processes that facilitate delamination. Some water soluble adhesives include those made by National Starch and Chemical company, Bostik Findley or the H.B. Fuller Company. If water soluble adhesives are used with a non-water permeable material films and non-water permeable coating on the cardboard applicator (such as wax), water can only reach the adhesive at the top of the applicator, the bottom of the film cap and windline on the applicator. In such a situation, holes or gaps may be created in the non-water soluble film or tube coating so that water can reach a greater adhesive area.

Cutting the topmost layer of paper of the cardboard applicator, during film trimming or as a separate step, may help facilitate delamination. This extended film trimming is typically a circumferential cut below the end of the film collar. This may be done by any known method, including cutting excess film with any blade, probe, knife laser, use of an air-knifing, water-knifing, or a heated knife or probe. The cuts may be made using pressure or combination of heat and pressure. The extended trimming effectively decouples the film cap from the top most layer of the paper allowing delamination.

Reducing the length of the film cap, thereby lessening the constricted tube surface area, may be used alone or in combination with other methods to facilitate delamination. Another way of improving and facilitating delamination is to create cuts in the film cap's collar portion that diminish the hoop stress in the collar thus facilitating delamination. All collar cuts are most efficient when they extend along the length of the collar, from the front or topside the applicator unit to the bottom of the film collar. The collar cuts may align with the areas of weakness in the film cap that form petals. Collar cuts may also align with the wind line or seam of the outer most paper layer of the applicator, although some embodiments may have collar cuts that may not align with the wind line or seam. Collar cuts may proceed from a point on the front or top edge of the applicator to a point where the bottom of the collar meets the wind line of the outermost paper. Some embodiments of collar cuts may be circumferential, connecting the wind line and collar cut.

VI. EXAMPLES a. Example 1

The Male Molding Process

An open ended flushable applicator is provided, which has two telescoping applicator units, the inserter tube and the pusher tube. Both applicator units have topside opposed to a bottom side. The topside of the inserter tube has an open end The male molding process can be accomplished by a thermoforming process described in detail below and a cold stretch forming process that is the same with the exclusion of the heating and vacuum steps. The resulting film cap from the cold stretch forming process has negligible thinning or plastic yielding at the top, and progressively increasing yielding, thinning or stretch in the direction of the collar portion, and less yielding, thinning or stretch at the bottom of the film cap.

In the male molding process, a male mandrel is obtained in the form of the cylindrical tampon with rounded top portion, is machined from Metapor BF 100 AL material, to a diameter just less than the interior diameter of the inserter tube. Due to the material's inherent porosity, the mandrel can be coupled with a vacuum source as desired. The bottom of the mandrel is left open to later contact a vacuum platen. The top of the mandrel has four slots cut and when the vacuum is applied, the film is drawn into these the slots during cap formation.

A block, which has in its center a vertical hole that has a slightly larger diameter and shorter length than the outer diameter and the length of the inserter tube, is also machined from the afore-mentioned Metapor material. In one typical execution, part of the mandrel is coated be coated to seal the surface pores with the exception of the surface of the bottom and the centered hole of the block so that the vacuum is only applied at the surface of the upper part of the mandrel The first applicator unit or inserter tube is placed over the mandrel, such that the bottom of the mandrel and the bottom side of the inserter tube are even such that part of the mandrel extends through the topside of the inserter tube.

The mandrel, inserter tube, and block are positioned on a vacuum platen. In preparation for forming the film cap, the vacuum platen is lowered such that when the film-holding fixture is swung down into the horizontal position, covering the mandrel and block, the top of the mandrel does not contact the bottom surface of the film.

Above the platen is a film-holding fixture that holds the film under tension and can be positioned over the mandrel-block assembly, to hold the film in a generally horizontal plane that is generally orthogonal to the vertical orientation of the mandrel-inserter combination within the block. Film is placed in this fixture. The film is heated to its softening point with a radiant thermal heater that is positioned above the surface of the film in the film fixture.

Then, the vacuum platen is raised as to push the forming fixture with the block and mandrel and inserter tube into the film. The film is then shaped around the top surface of the forming fixture, including the part of the mandrel that extends through the opening or part of the inserter tube. Typically, this is done with assistance from the vacuum being pulled through the forming fixture and in particular the slots on the top of the mandrel where the film is pulled into those slots. The formed film cap, around the exposed part of the mandrel and the top 18 mm of the inserter tube is then allowed to cool.

The combined inserter tube and mandrel arm then removed from the block with the formed film still attached. The hoop stress about the top 18 mm of the inserter tube may be sufficient to hold the film cap securely attached in place however, additional attachment means may be used, such as using adhesives before contacting the film to the mandrel-tube combination. For example, a spiral pattern of adhesive may be applied to the tube or the film such as Bostik Findley H2031 pressure sensitive adhesive at an average basis weight of 0.00093 grams/cm$^2$ may be placed on the top 7.5 mm of the tube. After the collar portion of the film cap is shaped around the upper part of the inserter tube, the film cap can be pressured into the adhesive to get a more secure attachment. The excess film is removed from around the film cap.

b. Example 2

The Female Molding Process

An open ended flushable applicator is provided, which has two telescoping applicator units, the inserter tube and the pusher tube. Both applicator units have topside opposed to a bottom side. The topside of the inserter tube has an open end.

A female mold is obtained comprising a multitude of cavities in the form of the cylindrical rounded tampon, or inserter tube, is machined from Metapor BF 100 AL material, to a diameter just greater than the external diameter of the inserter tube. The cavities of the female mold have typically rounded edges at the surface of the mold For example, the cavities may be 1.65 cm deep and have a curving cylindrical side wall with a curvature of 0.64 cm radius at the bottom of the side wall to transition at bottom surface with a 0.34 cm diameter, while the top of the side wall has a curvature of a 0.51 cm radius transitioning to top of the mold.

The female mold is connected to a vacuum thermo former, such as available from Formech Company, UK. Due to the material's inherent porosity, the mold can be coupled with a vacuum source as desired, or extra holes or slits may be made in the mold, to draw the vacuum through. For example, the cavities may have cross-pattern(s) at the bottom, through which the vacuum can be applied. The vacuum pulling and heating can be done as described above in the male molding process. The heating step may be done prior to, simultaneous with and subsequent to the vacuum step.

The 25 cm×25 cm film is held in a film holder in tension and placed above the openings of the mold, under the heat source. The radiant heat source is switched on to soften the film, for example for 3 seconds. Then, the vacuum source is switched on, pulling the softened film into the cavities. If the heating is done subsequent to the vacuum step, the film may be partially pulled into the cavities by vacuum, and is heated to pull the film even further into the cavities. The film is allowed to cool and the vacuum is switched off and may be assisted by passing of cold air over the film and mold.

The shaped film caps can then be removed from the female mold and cut loose from one another. They are then attached to the applicators, e.g. to the inserter tube's inside or outside cylindrical wall, typically by use of adhesives on the wall portion to be attached to the collar portion of the film cap, as described above. Excess film may be cut away. This process may be modified in many ways, including heating of the mold (rather than the film or in addition to the film), cooling of the mold (passing of cold fluids through the mold), combination use with a male mold (plug assist), different films, sizes, cavity-curvatures, etc.

What is claimed is:

1. A tampon and applicator arrangement comprising:
   a tampon, an applicator unit, and a film cap,
   said tampon having a withdrawal end opposed to an insertion end, said insertion end having a top portion;
   said applicator unit being capable of receiving said tampon, said applicator unit having a bottom side opposed to a topside;

said film cap attached to at least a portion of said applicator unit, said film cap being uniformly shaped and covering at least a portion of said top portion of said tampon;

wherein said film cap has areas of variable thickness, the variation in thickness being at least 20% from a first area to a second area;

said film cay having a top portion and a collar portion, wherein said collar portion is thinner than said tot portion.

2. The tampon and applicator arrangement according to claim 1 having at least about 20% of said tampon exposed at the average maximum film cap extension.

3. The tampon and applicator arrangement according to claim 1, said arrangement being cylindrical, and having said film cap with a top portion and with a collar portion; and said film cap having areas of weakness in the form of one or more continuous or discontinuous lines positioned from said top portion of the film cap toward said collar portion of the film cap.

4. The tampon and applicator arrangement according to claim 1, wherein the film cap comprises a formable film.

5. The tampon and applicator arrangement according to claim 1, wherein the film cap comprises a thermoplastic film.

6. The tampon and applicator arrangement according to claim 1, wherein the arrangement has maximum expulsion force to rupture said film cap and expel said tampon through said film cap, said maximum expulsion force ranging from about 700 grams-force to about 2500 grams-force.

7. The tampon and applicator arrangement according to claim 1 wherein said film cap has no folds, welds or seams.

8. the tampon and applicator arrangement according to claim 1 wherein the film cap has a collar portion and a dome-shaped top portion, wherein said top portion is more extensible or stretchable than the collar portion; and said collar portion is strain hardened.

* * * * *